(12) United States Patent
McErlean et al.

(10) Patent No.: US 9,700,379 B2
(45) Date of Patent: Jul. 11, 2017

(54) APPARATUS AND METHOD FOR DETERMINING A STATUS OF A MEDICAL DEVICE COMPONENT

(71) Applicant: Emblation Limited, Alloa (GB)

(72) Inventors: Eamon McErlean, Alloa (GB); Gary Beale, Alloa (GB)

(73) Assignee: EMBLATION LIMITED, Inglewood (GB)

( * ) Notice: Subject to any disclaimer, the term of this patent is extended or adjusted under 35 U.S.C. 154(b) by 267 days.

(21) Appl. No.: 14/397,784

(22) PCT Filed: Apr. 30, 2013

(86) PCT No.: PCT/GB2013/051104
§ 371 (c)(1),
(2) Date: Oct. 29, 2014

(87) PCT Pub. No.: WO2013/164597
PCT Pub. Date: Nov. 7, 2013

(65) Prior Publication Data
US 2015/0102825 A1    Apr. 16, 2015

(30) Foreign Application Priority Data
Apr. 30, 2012  (GB) .................................. 1207490.2

(51) Int. Cl.
*G01R 31/07*  (2006.01)
*A61B 19/00*  (2006.01)
*A61B 90/00*  (2016.01)
*A61B 90/90*  (2016.01)
*A61B 18/14*  (2006.01)
(Continued)

(52) U.S. Cl.
CPC .............. *A61B 19/44* (2013.01); *A61B 90/00* (2016.02); *A61B 90/90* (2016.02); *G01R 31/07* (2013.01); *A61B 18/14* (2013.01); *A61B 18/1815* (2013.01); *A61B 2017/00482* (2013.01);
(Continued)

(58) Field of Classification Search
CPC ...... G01R 31/002; G01R 31/07; G01R 31/08; G01R 31/31901; A61B 90/00; A61B 90/90; A61B 19/44; A61B 18/14; A61B 18/1815; A61B 2090/0803; A61B 2090/0814;
(Continued)

(56) References Cited

U.S. PATENT DOCUMENTS 5,688,232 A    11/1997  Flower
5,693,042 A    12/1997  Boiarski et al.
(Continued)

FOREIGN PATENT DOCUMENTS

EP    1943956    7/2008

OTHER PUBLICATIONS

International Search Report and Written Opinion dated Jul. 24, 2013 in Application No. PCT/GB2013/051104.

*Primary Examiner* — Hoai-An D Nguyen
(74) *Attorney, Agent, or Firm* — Snell & Wilmer L.L.P.

(57) ABSTRACT

An apparatus for determining a status of a medical device component is disclosed. The apparatus includes at least one fusible component to indicate whether the medical device component has been used, and at least one reference component having at least one reference property that is representative of the presence, identity or type of the medical device component. The reference component is non-fusible under ordinary operating conditions.

34 Claims, 13 Drawing Sheets

(51) Int. Cl.
   *A61B 18/18*   (2006.01)
   *A61B 17/00*   (2006.01)
(52) U.S. Cl.
   CPC ............... *A61B 2090/0803* (2016.02); *A61B 2090/0814* (2016.02)
(58) Field of Classification Search
   CPC ........ A61B 2017/00482; H01L 23/525; H01L 23/5252; H01L 23/5256; G11C 17/16
   USPC ....... 324/500, 507, 522, 525, 529, 537, 550, 324/555
   See application file for complete search history.

(56) References Cited

U.S. PATENT DOCUMENTS

| | | | |
|---|---|---|---|
| 2003/0154456 A1* | 8/2003 | Koike | H01L 27/0802 338/308 |
| 2008/0012624 A1* | 1/2008 | Kamatani | H01C 17/22 327/525 |
| 2009/0002119 A1* | 1/2009 | Nirschl | G11C 17/18 337/206 |
| 2010/0057069 A1 | 3/2010 | Ben-Nun | |
| 2010/0114259 A1 | 5/2010 | Herregraven et al. | |
| 2013/0053680 A1* | 2/2013 | Frey | A61B 6/12 600/411 |
| 2013/0131579 A1* | 5/2013 | Mantell | A61M 13/00 604/23 |

\* cited by examiner $$Rt = \frac{(R1 + Rf) * R2}{(R1 + RF) + R2}$$

Where $Rf < R1$ or $R2$ $$Rt = \frac{R1 * R2}{R1 + R2}$$

APPARATUS AND METHOD FOR DETERMINING A STATUS OF A MEDICAL DEVICE COMPONENT

CROSS-REFERENCE TO RELATED APPLICATIONS

This application is a U.S. national phase filing under 35 U.S.C. §371 of PCT/GB2013/051104 filed Apr. 30, 2013. PCT/GB2013/051104 claims priority from GB Application No. 1207490.2 which was filed on Apr. 30, 2012, all of which are incorporated herein by reference in their entirety.

FIELD OF THE INVENTION

The present invention relates to a method and apparatus for determining the status of a medical device component. The method and apparatus may be for preventing the reuse of the medical device component.

BACKGROUND TO THE INVENTION

In many invasive surgeries utilizing medical devices there is the requirement to use sterile medical devices, for example sterile instruments. This necessitates the use of products that on first use are sterile and subsequently disposed of, or re-sterilised for reuse. Ideally it should not be possible to reuse a medical device until it has been re-sterilised or in the case of single-use only device reuse should be prevented. This can be achieved by a number of means such as mechanically changing the component or utilizing materials that disintegrate after use or materials not compatible with high temperature steam sterilisation.

In some applications a disposable medical device component is connected to a main medical device that is reused. Typically the main medical device uses or controls the operation of the disposable component and as the disposable component represents a small portion of the overall system this part may be discarded to save cost and create a revenue stream. In order to maintain safety by preventing the use of unsterile or contaminated equipment and safeguard product revenue it is imperative to be able to prevent reuse of disposable components.

In some disposable medical products a range of electronic reuse mitigation measures have been described, often implementing complex methods such as RFID chips or polling multiple circuits or communicating with integrated circuits containing software to convey identification and status of the medical device to the controlling system. Whilst these are feasible, their use in a medical device is impeded by the stringent regulations governing the use of software which requires expensive and time consuming software validation activities to achieve the required compliance.

Another known approach to identifying use status for a variety of products is to utilise a onetime fusible element that is blown (open circuit) at the start of or during use. Whilst the use of fuses is practical and readily implemented generally they do not identify the device nor after being blown do they indicate their presence or the integrity of the connection. Thus, it could be possible for the device to be swapped mid-treatment resulting in cross-contamination or replacement of the fuse component.

SUMMARY OF THE INVENTION

In a first independent aspect of the invention there is provided apparatus for determining a status of a medical device component, wherein the apparatus comprises:—at least one fusible component to indicate whether the medical device component has been used, and at least one reference component having at least one reference property that is representative of the presence, identity or type of the medical device component, wherein the reference component is non-fusible under ordinary operating conditions.

The status may comprise at least one of whether the medical device component is present or absent from a main medical device; the identity of the medical device component; the type of the medical device component; whether the medical device component has been disconnected and, optionally, for how long or how many times; a length of time for which the medical device component has been used; a number of treatments performed using the medical device component.

By providing the fusible element and the non-fusible reference element a particularly simple, robust and reliable way of determining the status of a medical device component, whilst ensuring that the medical device component is not reused inappropriately, may be provided. Furthermore it can be ensured that operation of main medical device is tailored to the particular medical device component or type of medical device component.

The use of both fusible and reference components can provide for dual-state circuits that simultaneously indicate unused/used status and connected/disconnected presence resulting in three distinct identifiable states. The components may be arranged so that it is impossible to obtain the used status whilst the device is unconnected.

The at least one fusible component and the at least one reference component may be arranged in parallel.

The at least one fusible component and the at least one reference component may be arranged so that in operation the value of a measurement of a property is representative of a combination of a property of the at least one fusible component and said reference property of the at least one reference component.

The at least one fusible component and the at least one reference component may be arranged so that in operation it can be determined whether the at least one fusible component has fused from the value of a measurement of a property.

Optionally, if the at least one fusible component has been fused, said at least one reference property of the at least one reference element can be determined from the value of the at least one measurement.

The measurement of a property may comprise a single measurement.

Optionally, if the fusible component has been fused, the value of the at least one measurement may be representative of at least one of:—the presence of the medical device component; the identity of the medical device component; the type of the medical device component The value of the least one measurement may be useable to identify the device from a series or family of instruments to allow for bespoke operation, for example a device specific lifetime or function such as energy output or force. This can be achieved by using the connection identification to convey additional information that is specific to that device and can then be used to tailor performance.

The measurement may comprise a measurement of at least one of resistance, capacitance, impedance, breakdown voltage, bias, frequency response, time constant, or delay.

There may be a measurement path that passes through the at least one reference component. The fusible component when not fused may provide a short circuit or low resistance path in the measurement path across the or at least one of the reference components, and the short circuit or low resistance path may be removed when the fusible component is fused.

In operation, the at least one measurement may be performed via the measurement path.

The measurement path may be a measurement path between a set of measurement points. The set of measurement points may comprise a single measurement point or a plurality of measurement points. The plurality of measurement points may comprise a pair of measurement points.

The set of measurement points may be at the apparatus or the medical device component The set of measurement points may be at a main medical device to which the medical device component is connectable, and the measurement path may be formed when the apparatus is connected to the main medical device.

The measurement path may include at least one further component. The at least one further component may, for example, be located within the apparatus or within the main medical device.

The reference property may comprise at least one of resistance, capacitance, impedance, breakdown voltage, bias, frequency response, time constant, or delay.

The reference component and/or the fusible component may comprise at least one of a resistor, a capacitor, a diode, a battery, a passive or active element, a semiconductor device or a combination thereof.

The apparatus may be incorporated in the medical device component.

The medical device component may comprise a detachable and/or disposable component, for example an applicator, for instance a microwave applicator or an electrosurgery applicator.

The medical device component may comprise a component that, in normal operation comes into contact with a patient's body.

The medical device component may be attachable to a main medical device. The main medical device may comprise at least one of a handpiece or connection terminal connected via cabling to a main controlling system. The main medical device may comprise at least one of a microwave source, an ultrasound source, a visible light source, an infrared source, or an electrosurgery apparatus.

The apparatus may further comprise a controller comprising a processing resource that is configured to perform an algorithm for determining a status of the medical device component from at least one measurement performed on the at least one fusible component and/or the at least one reference component.

In another independent aspect of the invention there is provided a control apparatus for determining the status of a medical device component, the control apparatus being connectable to, or comprised within, an apparatus for determining status as claimed or described herein, and comprising a processing resource that is configured to perform an algorithm for determining a status of the medical device component from measurement performed on the at least one fusible component and/or the at least one reference component.

The status may comprise at least one of whether the medical device component is present or absent from the main medical device; the identity of the medical device component; the type of the medical device component; whether the medical device component has been disconnected and, optionally, for how long or how many times; the length of time for which the medical device component has been used; a number of treatments performed using the medical device component.

The processing resource may comprise hardware and/or software. The algorithm may be implemented in software or in hardware and may provide for robust operation.

The apparatus may further comprise measurement circuitry for performing the at least one measurement, for example measurement circuitry for performing electrical and/or magnetic measurements.

The measurement circuitry may be configured to perform the at least one measurement via the measurement path.

The medical device component may be connectable to a main medical device and the algorithm may be configured to control operation of the main medical device in dependence on the determined status of the medical device component.

The apparatus may further comprise a data store storing data representative of the value of the at least one reference property. The controller may be configured to compare a value of the at least one measurement to data stored in the data store to determine the status of the medical device component.

The controller may be configured to at least one of determine if the medical device component has been connected or disconnected, or determine if the medical device component has been used or is unused; and to control operation of the main medical device in dependence on the determination.

The controller may be configured to determine whether the fusible element has been fused and prevent use of the main medical device if the fusible element has been fused.

The controller may be configured to determine whether the medical device component has been used and prevent reuse of the medical device component.

The controller may be configured to determine whether the fusible element has been fused, and if the fusible element has not been fused to apply a signal to fuse the fusible element.

The apparatus may comprise a current source, or other signal source, for applying the signal.

The controller may be configured to identify the type or identity of the medical device component and to select at least one operating parameter in dependence on the type of identity of the medical device component.

The apparatus may further comprising monitoring means, for example a monitor, for monitoring at least one of the length of time the medical device component has been used or has been useable, for example the length of time since the medical device component was attached to the main medical device and/or the length of time since the fusible component was fused, or the number or length of treatments performed using the medical device component.

The algorithm may be configured to monitor the length of time the medical device component has been used or has been useable, for example the length of time since the medical device component was attached to the main medical device and/or the length of time since the fusible component was fused.

The algorithm may be configured to monitor the number or length of treatments performed using the medical device component.

The algorithm may be configured to allow use of the medical device component for a selected period of time or for a selected number of treatments.

The algorithm may be configured to prevent normal operation of the main medical device and/or the medical device component in response to expiry of the selected period of time and/or in response to performance of the selected number of treatments.

The controller may be configured to monitor disconnection of the medical device component from the main medical device and to allow disconnection for times shorter than a selected time period without preventing operation of the main medical device.

In a further independent aspect of the invention there is provided a system for controlling or preventing reuse of a medical device component, comprising apparatus for determining a status of the medical device component, and a housing for housing the apparatus.

The housing may comprise a lockable cover. Thus, a user may be inhibited from removing, resetting or otherwise interfering with components of the apparatus.

In another independent aspect of the invention there is provided a method for determining a status of a medical device component, wherein the method comprises performing a measurement via a measurement path, the measurement path comprising at least one fusible component to indicate whether the medical device component has been used, and at least one reference component having at least one reference property that is representative of the presence, identity or type of the medical device component, wherein the reference component is non-fusible under ordinary operating conditions.

The at least one fusible component and the at least one reference component may be arranged in parallel.

The at least one fusible component and the at least one reference component may be arranged so that in operation the value of a measurement of a property is representative of a combination of a property of the at least one fusible component and said reference property of the at least one reference component.

The method may further comprise determining whether the at least one fusible component has fused from the value of the measurement.

The method may further comprise, if the at least one fusible component has been fused, determining said at least one reference property of the at least one reference element from the value of the at least one measurement.

The method may further comprise, if the fusible component has been fused, determining from the value of the at least one measurement at least one of:—the presence of the medical device component; the identity of the medical device component; the type of the medical device component.

The measurement may comprise a measurement of at least one of resistance, capacitance, impedance, breakdown voltage, bias, frequency response, time constant, or delay.

The fusible component when not fused may provide a short circuit or low resistance path in the measurement path across the or at least one of the reference components, and the short circuit or low resistance path may be removed when the fusible component is fused.

The method may comprise performing an algorithm for determining a status of the medical device component from the at least one measurement.

The method may comprise at least one of determining if the medical device component has been connected or disconnected, or determining if the medical device component has been used or is unused, and controlling operation of a main medical device in dependence on the determination.

The method may comprise determining whether the fusible element has been fused and preventing use of the main medical device if the fusible element has been fused.

The method may comprise determining whether the medical device component has been used and preventing reuse of the medical device component.

The method may comprise determine whether the fusible component has been fused, and if the fusible component has not been fused applying a signal to fuse the fusible component.

The method may comprise identifying the type or identity of the medical device component and selecting at least one operating parameter in dependence on the type of identity of the medical device component.

The method may comprise monitoring the length of time the medical device component has been used or has been useable, for example the length of time since the medical device component was attached to the main medical device and/or the length of time since the fusible component was fused.

The method may comprise monitoring the number or length of treatments performed using the medical device component.

The method may comprise allowing use of the medical device component for a selected period of time or for a selected number of treatments.

The method may comprise preventing normal operation of the main medical device and/or the medical device component in response to expiry of the selected period of time and/or in response to performance of the selected number of treatments.

The method may comprise monitoring disconnection of the medical device component from the main medical device and allowing disconnection for times shorter than a selected time period without preventing operation of the main medical device.

In another independent aspect of the invention there is provided a method and apparatus intended for determining the presence, status and preventing reuse of a medical device. The apparatus comprising a single use or disposable medical device having:—a fusible component to indicate unused/used status; a reference component connected in parallel with the fusible component indicating the continued presence of the disposable component to a main medical device. wherein:—the reference component has a unique electrical characteristic used to identify the type or family of the device.

In one embodiment, the reference component may comprise a resistor, capacitor, diode battery or other passive, semiconductor or active element or network of such elements creating a unique resistance, capacitance, impedance, breakdown voltage, bias, frequency response, time constant, delay or other electrical characteristic.

In another embodiment the reference component may be revealed upon the fusible component becoming opened and may form part of a circuit in series or parallel with at least one secondary element to provide a unique electrical characteristic. The secondary elements may reside within the main device that houses the disposable device or may be reside inside a controlling system that communicates with the reference component.

In a further, independent aspect of the invention there is provided an algorithm known as the controlling algorithm, enacted in software or hardware to identify if the disposable device has been connected or disconnected or has be used or is unused and control the operation of the main medical device based upon these inputs.

In one embodiment, the controlling algorithm in the initial state and upon first connection of the disposable component may verify the presence of a short circuit or small resistance indicating an intact fuse prior to commencement. The controlling algorithm may interpret measurements other than a short circuit or small resistance as a used device and will prevent reuse. The algorithm may control the main medical device to deliver a current greater than the rated fuse current for a sufficient period to inactivate (open/blow) the fuse preventing the device from being reused.

In another embodiment, the controlling algorithm that may check for the presence of the reference component (connected in parallel with the fuse) becoming apparent upon the fuse opening to verify the correct function of the fuse before proceeding.

In an alternative embodiment, the controlling algorithm may check for the presence of reference components connected in parallel and/or in series with the fuse as a means of identification. The combination of components may present an identity that changes when the fuse opens. In this embodiment one reference component may be combined with others connected in series or parallel to create a unique reference value. By changing any one of the reference components the combined reference value may be easily changed. Likewise variation of the intrinsic electrical properties of the fuse may be accommodated by using supplementary components to mask or reduce the effects of these variations.

The apparatus may further comprise a controlling algorithm that checks for the continual connection of the disposable component by monitoring for the presence of the reference component. The reference component may produce or influence a measurement of voltage, current, impedance, time constant, delay, frequency response, breakdown voltage, bias, or other electrical performance that can be measured for the purposes of monitoring the connection status.

Advantageously, the controlling algorithm may additionally use the reference to identify the applicator type which may allow the controlling algorithm to select specific performance characteristics or make reference to preloaded treatment parameters dependent upon the identity derived for the attached disposable component based upon the reference measured.

In an alternative embodiment, the controlling algorithm may check for the presence of reference components connected in parallel and/or in series with the fuse as a means of identification. The combination of components may present an identity that changes when the fuse opens. In this embodiment one reference component may be combined with another's connected in series or parallel to create a unique reference value. By changing one of the reference components the combined reference value may be easily changed in application requiring the identification of multiple devices.

In an alternative embodiment the controlling algorithm may accommodate or ignore brief changes or removals of this reference created as a result of intermittent connection or interference to enhance reliability. In addition the controlling algorithm may also cause the treatment to stop or alternatively continue until the button is released.

The apparatus may further comprise a controlling algorithm that upon sensing connection of the disposable component may start a counter (functional lifetime) for that device which may be controlled by the user or may be run continuously whilst the device is connected until the predetermined device lifetime expires or until the treatment completes before returning the algorithm to the initial state rendering the disposable component inactive. The counter may be created in hardware or software and may comprise a number of synchronous counters compared for safety.

In an alternative embodiment the controlling algorithm may also contain a plurality of counters running either sequentially or in a nested configuration to control various stages or parameters of operation, one example being an operating duration counter (delivery/burst) being nested inside an overall treatment duration counter (lifetime).

In another embodiment, the controlling algorithm may also interpret removal or changes of the reference over a specified time duration as a disconnection of the disposable medical device returning the algorithm to the initial state and awaiting connection of a new device.

The apparatus may further comprise a counter that provides a period of time in which the applicator status may be acquired and checked before proceeding to blow the fuse thus preventing the inadvertent deactivation of working devices.

In a further, independent aspect of the invention there is provided a method and apparatus for high volume manufacturing of a compact reuse mitigation device.
having:—
a fusible component;
a reference component connected in parallel with the fusible component;
a mounting arrangement connecting each component The apparatus may comprise a fusible component such as a discrete fuse being soldered or bonded directly onto the reference component in a parallel connection arrangement.

The apparatus may further comprise a fusible component located on one side of a printed circuit board (PCB) with a reference component connected in parallel with the fusible component on the same side or connected by via to the opposite side of the PCB In another embodiment, the fusible component may be a thin printed conductor or a discrete surface mount fuse component with a reference component connected in parallel with the fusible component on the same side or connected by via to the opposite side of the PCB.

In a further embodiment, the reference component may be a thin printed element such as a printed inductor or printed capacitor.

The apparatus may be compatible with manufacture using mass production techniques, and thus may be suitable for high volume applications.

In a further, independent aspect of the invention there is provided a method for housing a reuse mitigation device possessing robust connection means and preventing user tamper. The apparatus may have a reuse mitigation device; a locating means; a locking cover containing access features.

In one embodiment the housing may have a locating means that comprises a recessed molded platform of ribs to locate and support the reuse mitigation component.

In another embodiment, the housing may be located in a machined or molded pocket or cut out portion of a body.

The apparatus may further comprise a tamperproof covering with ramped or barbed features that provide a locking means upon insertion or placement of the cover.

In another embodiment, the cover may be manufactured to possess a mechanical weakness that upon tamper would fail causing retention of the locking means and failure of the covering preventing replacement of the reuse mitigation device In another embodiment, the housing may be manufactured to possess weakness that upon tamper would cause failure of the locking means preventing replacement of the covering.

The apparatus may further comprise access features in the locking cover to permit access to contactable conductor areas on the reuse mitigation device.

In one embodiment the reuse mitigation device may be contacted by a self biasing pin (pogo pin), conductive spring, conductive elastomer or other self biasing electrical contact.

Such connection means can accommodate manufacturing tolerances and typical forces or conditions applied during use, providing for robust and reliable operation, and can use a minimum number of interconnecting contacts.

There may also be provided an apparatus or method substantially as described herein with reference to the accompanying drawings. It should be understood that the embodiments described herein are merely exemplary and that various modifications may be made thereto without departing from the scope of the invention.

One example of a scenario incorporating the inventions may be in an Rf/microwave applicator for an invasive ablation or hyperthermia treatment. This type of device may be intended only to function once with the treatment profile being related to the identity of the device. Upon connection to a handpiece or system the device would trigger a stored profile to be executed. This profile would contain information such as the treatment duration, power delivered, frequency of operation, reflected power settings duration of the treatment, lifetime of the device, number of power cycles, number of permitted disconnections, disconnection duration and other information relevant to a microwave treatment.

Upon connection the system would recognize a new applicator and identify this to the user. Sometime after connection, or during or after a treatment the fuse would be blown to indicate that the device had been used. During the treatment the system would sense the disconnection of the device and take appropriate action depending upon the length of time the device was disconnected for. This could happen before or after the fuse had been blown. The system may permit limited use or reuse of a device for a patient such that adjustment may be made during the treatment including removal or cleaning of the disposable device for a time period.

Another example of a scenario may be in an automated tissue probe. In this application a tissue probe may be used to measure or sample tissue to extract or measure various parameters for analysis purposes. Upon connection to a system the device would identify its self as being new/unused or used, with this type of device intended only to function once to prevent cross-contamination.

Sometime after connection, or during or after use the fuse would be blown to indicate that the device had been used. During use the system would sense the disconnection of the device and take appropriate action depending upon the length of time the device was disconnected for. This could happen before or after the fuse had been blown. The system may permit limited use or reuse of a device for a patient such that adjustment may be made during the treatment including removal or cleaning of the disposable device for a time period.

Aspects and embodiments of the invention may employ a robust electronic design to create a reliable and easily validated hardware system that enables reuse of medical device components to be controlled or monitored.

Any feature of one aspect or embodiment of the invention may be applied as a feature of any other aspect or embodiment of the invention, in any combination.

DETAILED DESCRIPTION OF EMBODIMENTS

Embodiments of the invention are now described, by way of non-limiting example, and are illustrated in the following figures, in which:—

FIG. 1 is a schematic illustration of a system for detecting presence/status/identity and reuse using various electrical characteristic according to some embodiments of the invention;

FIGS. 2(a) and 2(b) represent schematic illustrations of arranged networks of reference elements creating a presence/status/identity and reuse prevention circuit according to some embodiments of the invention;

DETAILED DESCRIPTION OF EMBODIMENTS

Reference will now be made in detail to presently preferred compositions or embodiments and methods of the invention, which constitute the best modes of practicing the invention presently known to the inventors. However, it will be understood by those skilled in the art that the claimed subject matter may be practiced without these specific details. In other instances, well-known methods, procedures, components, and circuits have not been described in detail so as to not obscure the claimed subject matter.

In the following detailed description, reference is made to the accompanying drawings which form a part hereof, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Figure 1:
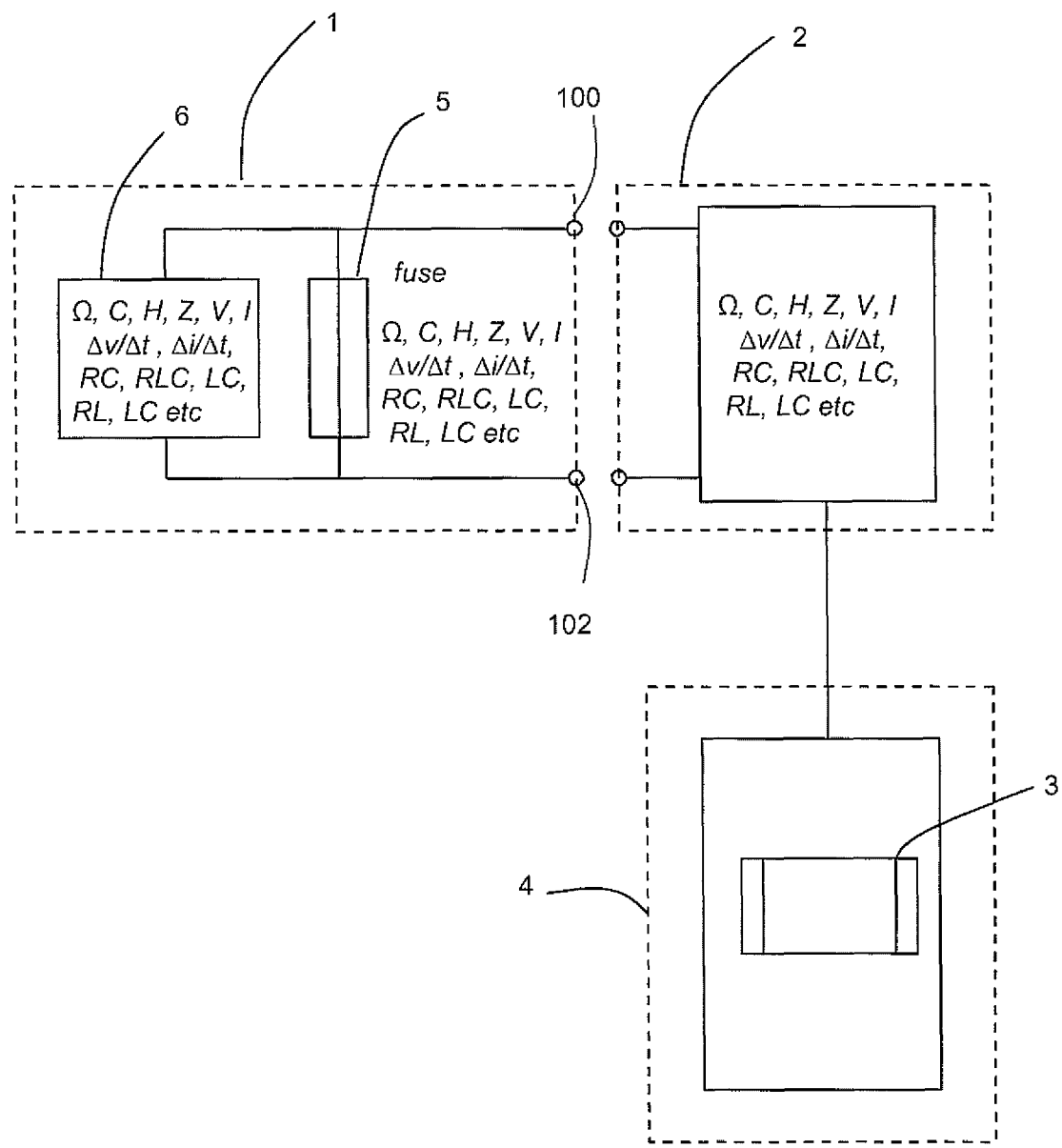

A system for detecting presence/status identity and preventing reuse of medical devices using various electrical characteristic is illustrated in FIG. 1. In this system there is a medical device component comprising a replaceable circuit 1 connectable to an intermediary component 2 and controlled by a hardware or software algorithm 3 located within a controller 4 forming part of a main medical device and connected to or integrated with the intermediary component 2. The controller 4 can also include measurement circuitry for performing measurement, for example measurements of electrical or magnetic properties.

The replaceable circuit 1 has a fusible element 5 to indicate current status and a reference element 6 to confer removal status and unique identity. The reference element 6 is non-fusible under normal operating conditions.

The replaceable circuit includes two terminals 100, 102 and the fusible element 5 and the reference element 6 are arranged on a measurement path between the two terminals 100, 102. In this case, the fusible element 5 and the reference element 6 are arranged in parallel and the measurement path can be considered to comprise two parallel branches, one passing through the fusible element 5 and one passing through the reference 6.

The measurement path may also be considered to include the intermediary component 2, which may include one or more secondary electrical or magnetic components, when the removable component 1 is connected to the intermediary component 2.

Using these parameters it can be determined if the connected device is new, has been used, is a particular type, or has been removed during operation. This knowledge may be used to control a treatment or prevent reuse of an expired product.

The reference element 6 may be a component or network of components that possesses a reference property, for example any suitable electrical or magnetic property such as resistance ($\Omega$), capacitance (C), inductance (H) impedance (Z), breakdown voltage (V), bias (V), current (I) frequency response (RLC) (LC), time constant (RC, RL) delay (RC, RL) or any other electrical or magnetic characteristic. The system may also make use of other electrical characteristics of the fuse 5 in conjunction with the reference element. The intermediary component 2 may also possess electrical properties that may be combined in series or parallel the with electrical properties of the replaceable circuit 1.

The reference property of the reference element 6 may be representative of the presence, identity or type of the medical device component.

In operation, measurement of a property, for example a suitable electrical or magnetic property, via the measurement path can be used to determine whether the fusible element has been fused and, if the fusible element has been fused, whether the medical device component is present or absent, the identity of the medical device component, or the type of the medical device component.

For example, in the embodiment of FIG. 1, the fusible element may be an element having a low electrical resistance when not fused, whereas the reference element may be a resistor having a high electrical resistance whose value is known. The known value of the electrical resistance of the reference element may be stored by the controller 4, which may also store data associating that value of electrical resistance with a particular medical device component or type of medical device component.

In operation, a measurement of, in this case, electrical resistance is performed via the measurement path. If the fusible element 5 is not yet fused then the measurement will indicate a low value of electrical resistance. It will be understood that in this case the measurement will represent a combination of the electrical resistance of the reference element 6 and the fusible element 5, but as the fusible element 5 effectively provides a short circuit or low resistance path the value of the measurement will primarily represent the value of the resistance of the fusible element 5. The controller 4 is able to determine from the measurement that the fusible element 5 has not been fused.

The controller 4 may then cause the fusible element to be fused, by causing a suitable current or other signal to be applied to the fusible element, to indicate that the medical device component has been or is about to be used. Subsequent measurements of the electrical resistance via the measurement path produce a value that is representative of the known resistance value of the reference element. Such measurements may produce a value that is equal to the known resistance value of the reference element (for example if substantially no other resistive components are in the measurement path) or may produce a value that is equal to the resistance value of the reference element in combination with other electrical components. The controller 4 may store the values of those other electrical components and can determine from the measurement value the resistance value of the reference element taking into account the resistance values of the other electrical components.

The controller 4 then determines the identity or type of the medical device component from the measurement value, which is representative of the resistance value of the reference component. The controller 4, in certain embodiments, may compare the measurement value to reference values stored in a look-up table or other data store in order to determine the identity or type of the medical device component.

In one mode of operation, the controller 4 controls operation of the main medical device in dependence on the identity or type of the medical device component determined from the measurement. For example, a treatment program or set of treatment parameters may be selected from a stored set of such treatment programs or set of treatment parameters in dependence on the identity or type of medical device component. Alternatively or additionally, the controller 4 is able to monitor and/or control the number, type or duration of treatments applied using the medical device component from the time the fusible element is fused. The controller 4 is able to determine that the medical device component is not removed or replaced following the initial fusing of the fusible element by repeating the measurement via the measurement path, for example on a continuous or periodic basis, or on command.

By providing the fusible element and the reference element in the measurement path a particularly simple, robust and reliable way is provided of ensuring that a medical device component is not reused inappropriately. Furthermore it can be ensured that operation of the main medical device is tailored to the particular medical device component or type of medical device component.

Figure 2:
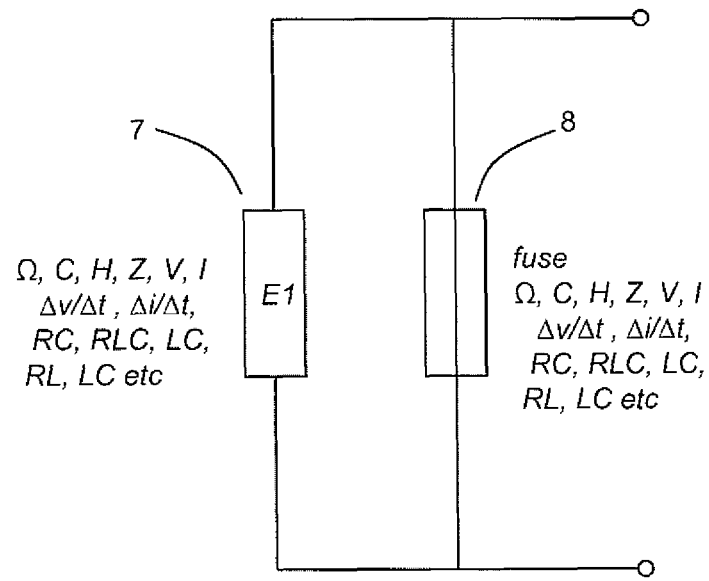
Figure 2:
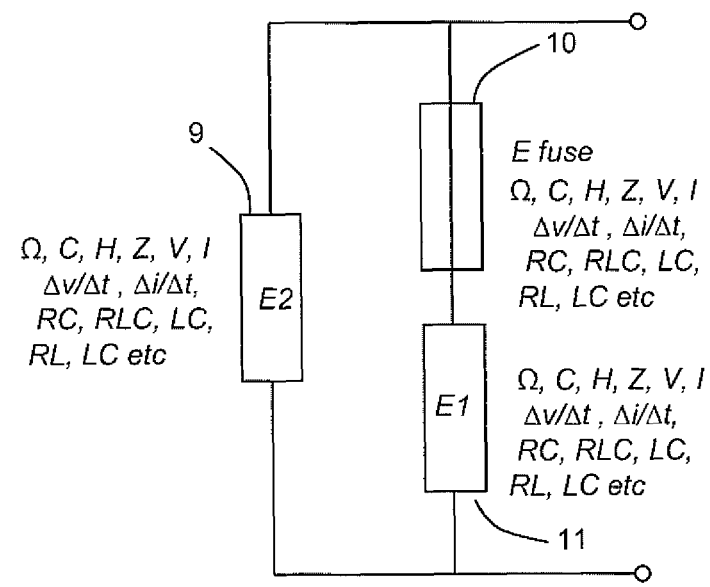

Referring to FIG. 2(*a*) a further embodiment of a replaceable circuit is illustrated. In this example a reference element 7 is connected in parallel with a fusible element 8. Upon destruction of the fuse the reference element becomes apparent and the electrical properties of the reference element 7 may be used to convey identify and removal status relating to the replaceable circuit to the controlling system.

Referring to FIG. 2(*b*) an alternative embodiment of a replaceable circuit is illustrated. In this example a reference element 9 is connected in parallel with a fusible element 10 and another reference element 11. In this arrangement the series and parallel electrical properties of both reference elements may be combined with the electrical properties of the fuse. The benefits of this are to reduce or mask the effects of variations of the fuse's electrical characteristics and additionally to provide flexibility in identifying the replaceable connectable component.

Figure 3:
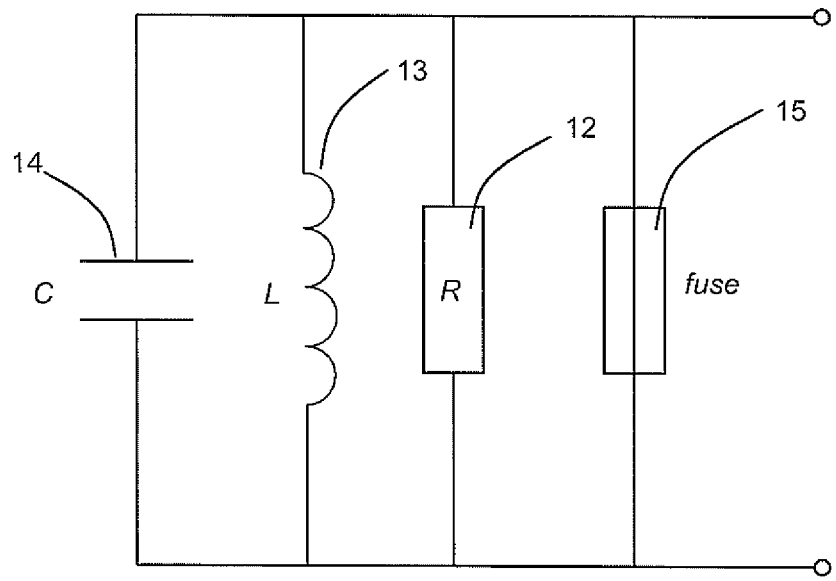
FIG. 3 is a schematic illustration of a network of reference elements creating a resonant circuit based presence/status/identity and reuse prevention circuit according to some embodiments of the invention.

Other embodiments of a replaceable circuit are illustrated in FIG. 3 which describes a RLC network arrangement 12, 13, 14 in parallel with a fuse 15. In this embodiment the reference element is a combined network of components having a resonant frequency depending upon the values of the components chosen. Upon the destruction of the fuse the circuit would transition to an RLC circuit introducing the damping resistor 12 which would change the performance of the resonant circuit.

Figure 4:
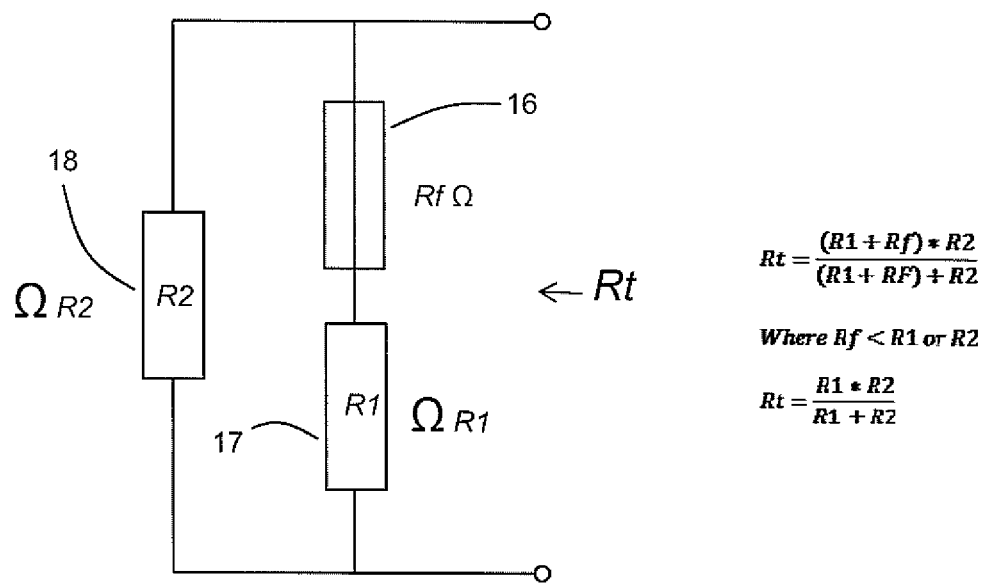
FIG. 4 is a schematic illustration of a network of resistor elements creating a presence/status/identity and reuse circuit according to some embodiments of the invention.

Referring to FIG. 4, an example of an embodiment of a replaceable circuit using resistors is illustrated. In this example the resistance seen looking into the circuit is a combination of the fuse resistance Rf 17 in series with the R1 18 all in parallel with the R2 16. When Rf is small in comparison to R1 or R2 the effect of Rf will be negated thus accommodating manufacturing tolerances associated with the fuse resistance Rf that may affect the identity of the replaceable circuit. Likewise the values of R1 or R2 may be chosen to be of high tolerance to minimise variation that could confuse the identity of the component.

Figure 5:
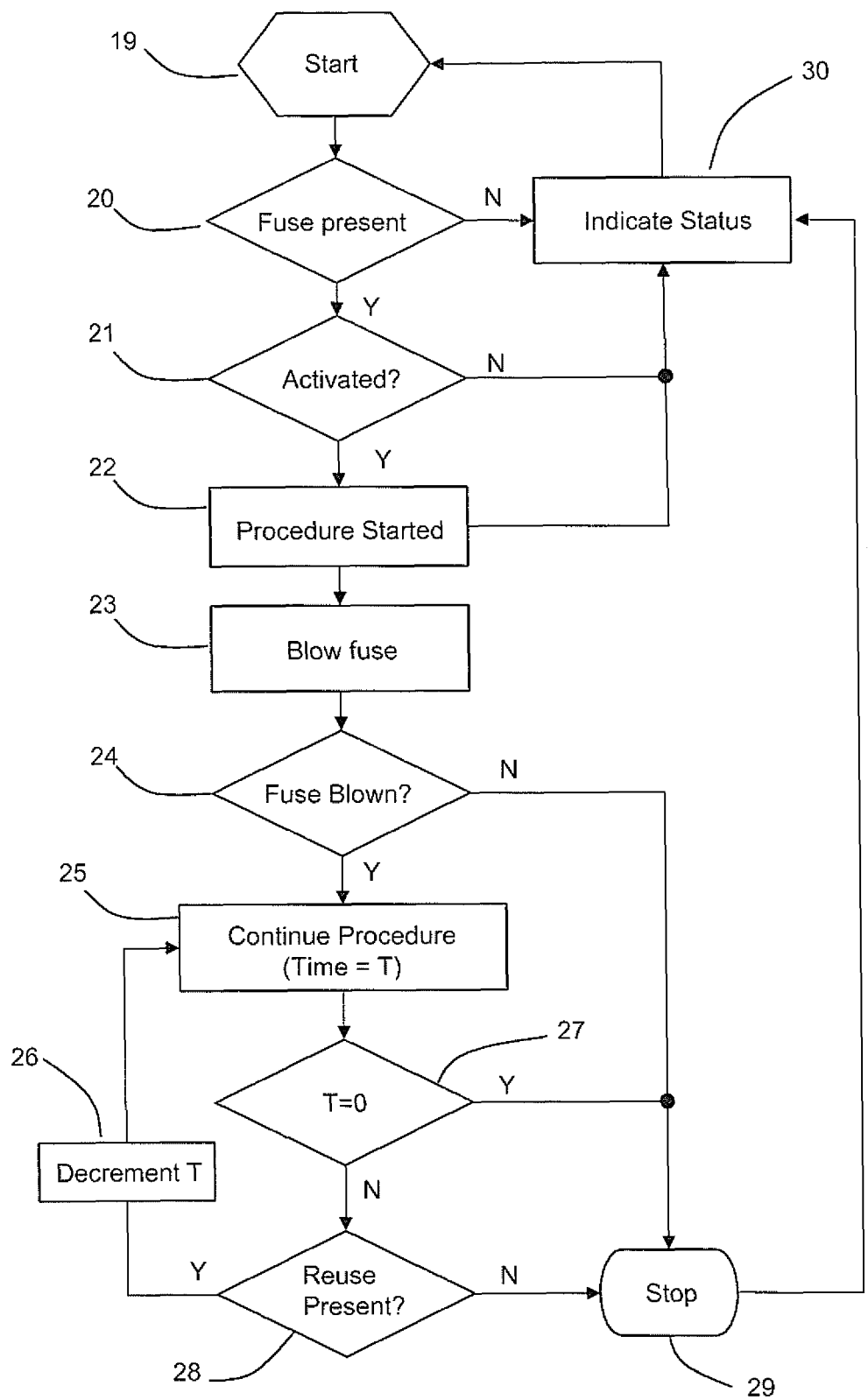
FIG. 5 is a flow chart of a process or algorithm for controlling a presence/status/identity and reuse prevention circuit according to some embodiments of the invention.

Referring to FIG. 5, a flowchart of an embodiment of control algorithm is described. This embodiment begins with the controller being activated 19 then checks for the presence of a fuse 20. If the fuse is absent the status reflects this 30 and the system awaits a new fuse 20, if the fuse is present the controller waits until the user activates the procedure 21 and updates the status 30 to reflect the presence of the fuse.

Upon activation of the treatment 21 the procedure 22 is started, the status 30 is updated and the controller blows the fuse 23. The controller verifies that the fuse is blown 24. If the fuse has not been blown the procedure is stopped 29 and the status 30 is updated accordingly. If the fuse is verified as being blown 24 and the reference component, also referred to as a reuse mitigation component, is present 28 the treatment continues for a set duration 25 (T) and is decremented 26 until the duration time is expired 27 (T=0) and the procedure is stopped 29 whereupon the status 30 is updated accordingly. During the procedure the presence of the reuse mitigation component is checked continuously 28 and if at any point the reuse mitigation component is not present the procedure stops 27 and the status 30 is updated accordingly.

Figure 6:
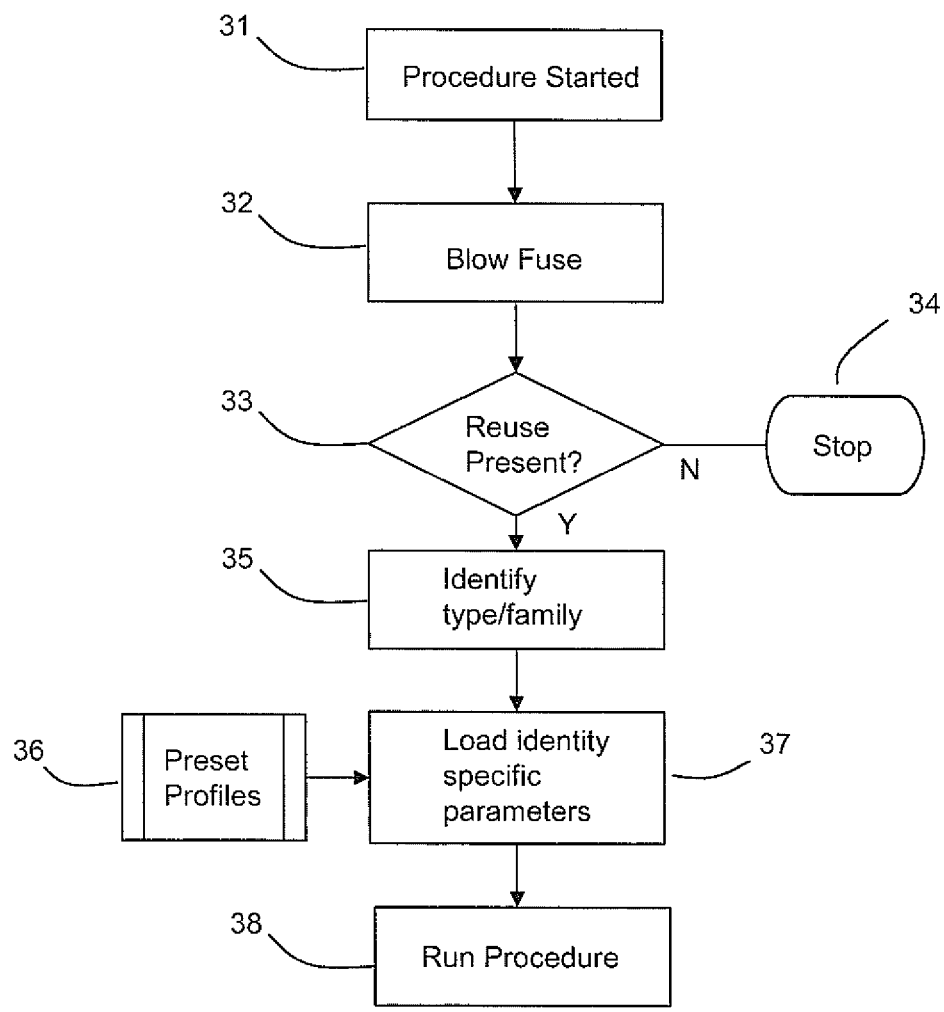
FIG. 6 is a flow chart of a sub-process or algorithm for controlling a presence/status/identity and reuse prevention circuit according to some embodiments of the invention.

Referring to FIG. 6, a flowchart of an alternative embodiment of control algorithm is presented where the reuse mitigation component is identified from measurement of electrical or magnetic properties, with this identity used to load specific treatment parameters. This embodiment begins where the procedure is started 31 then the fuse 32 is blown. The presence of the reuse mitigation component is checked 33 and if unavailable the procedure is stopped 34. Using the identity 35 of the reuse mitigation component the type or family of the device is selected 35 and used to load specific treatment data 37 from predetermined profiles 36 before executing the loaded procedure. These parameters could take the form of power/energy levels, durations, uses, treatment modes or cycles or other factors affecting a treatment.

Figure 7:
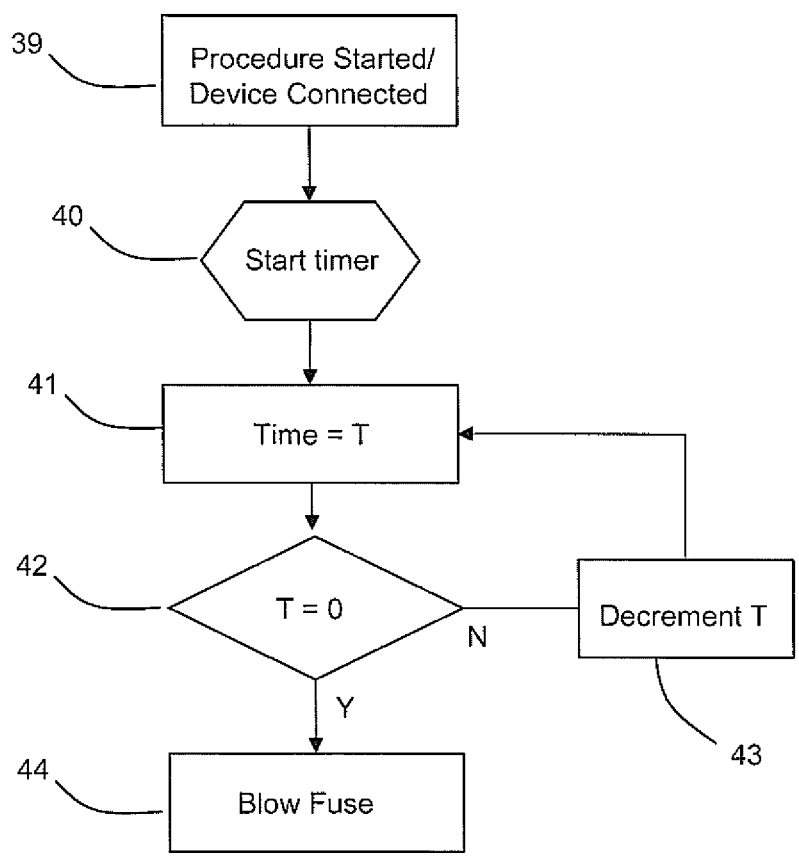
FIG. 7 is a flow chart of a sub-process for controlling the timing of a fuse blowing circuit within the process or algorithm of FIG. 5 according to some embodiments of the invention.

Referring to FIG. 7, a flowchart of an alternative embodiment of control algorithm is presented where the algorithm applies a delay prior to blowing the fuse. This embodiment begins where the procedure is started 39 alternatively this also may be when a device is connected. A timer 40 begins and counts a time 41 (T) until the time has elapsed (T=0) 42. Until the time has elapsed the time 41 (T) is decremented 43. When the timer has elapsed 42 the fuse is blown 44. This embodiment is advantageous in that it prevents the device being instantly deactivated should the user wish to delay commencing a treatment without unnecessarily deactivating an unused device.

Figure 8:
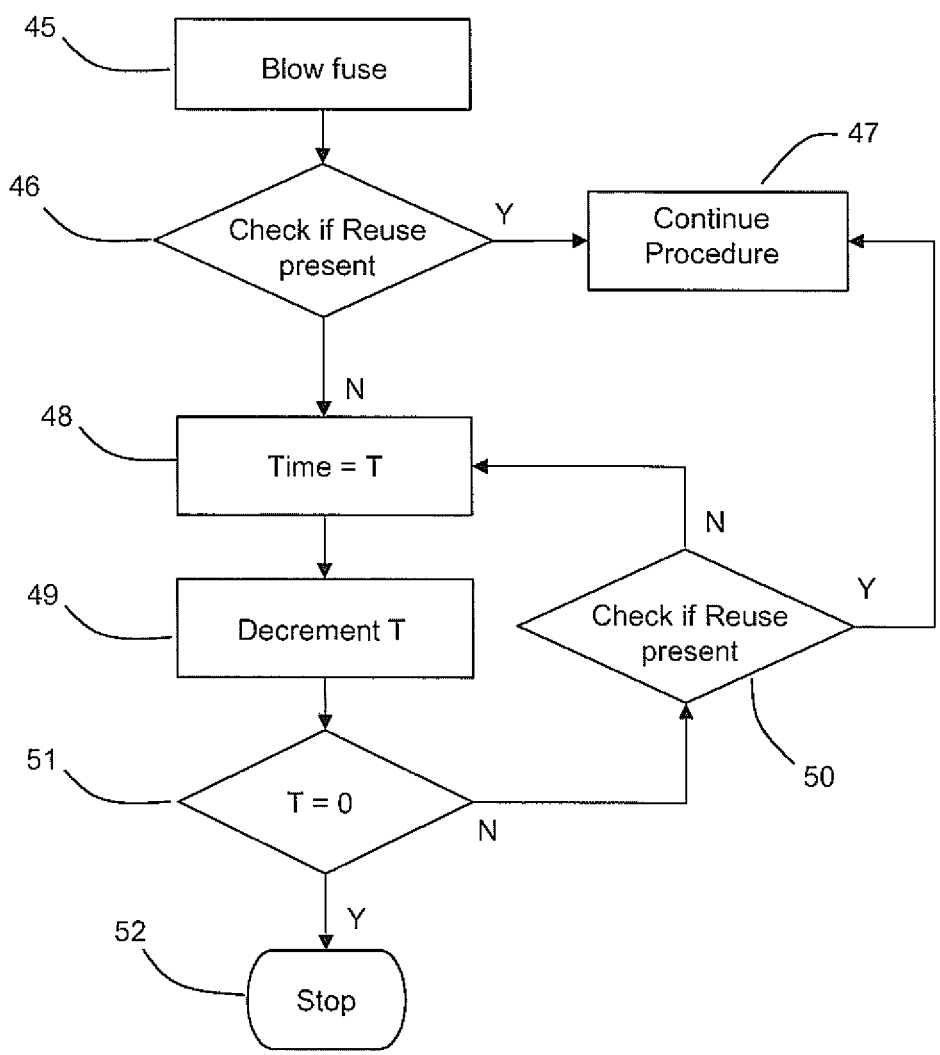
FIG. 8 is a flow chart of a sub-process for controlling the timing of a reuse removal checking circuit within the process or algorithm of FIG. 5 according to some embodiments of the invention.

Referring to FIG. 8, a flowchart of an alternative embodiment of control algorithm is presented where the removal of the reuse mitigation component for a duration is accommodated. This embodiment begins where the fuse has been blown 45 and the reuse mitigation component is verified as being present 46, and when present the procedure continues 47. When it cannot be verified that the reuse mitigation component is present a timer 48 starts. The timer runs 49 until it has expired 50 and the procedure is halted 51. If the reuse mitigation component is presented 50 before the timer expires the procedure is resumed 47. The timer may alternatively be realised in hardware such as a capacitive discharge, RC circuit or other time constant. Advantageously the time could be brief enough to accommodate the possibility of an intermittent connection to the reuse mitigation component for example lasting a number of milliseconds such that this does not prevent a procedure being inadvertently stopped. In an alternative embodiment the time duration may be long enough to enable a treatment to be paused should the device require removal for attention, such as cleaning or adjusting or any other reason. The time duration can be controlled to prevent reuse across multiple patients in the same day or any duration required.

Figure 9:
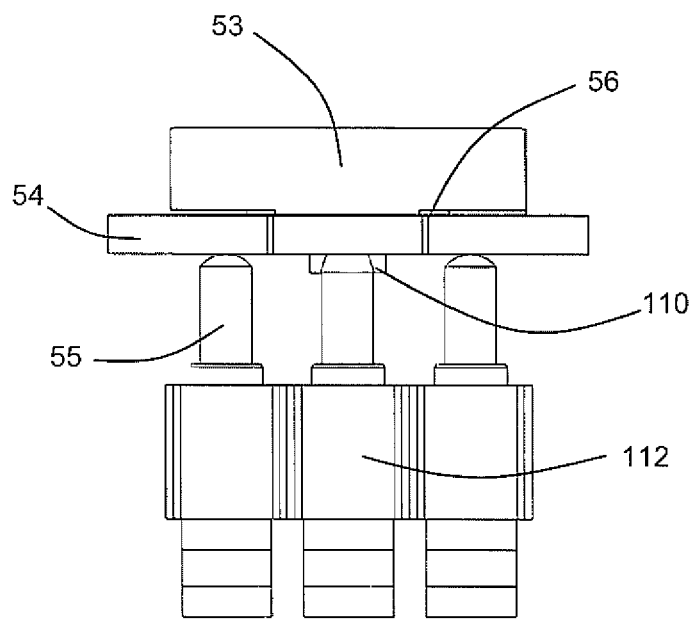
FIG. 9(a) is a schematic diagram of a presence/status/identity and reuse prevention circuit including the connection means according to some embodiments of the invention.
FIG. 9(b) is an alternative view of the diagram in FIG. 9(a)
Figure 9:
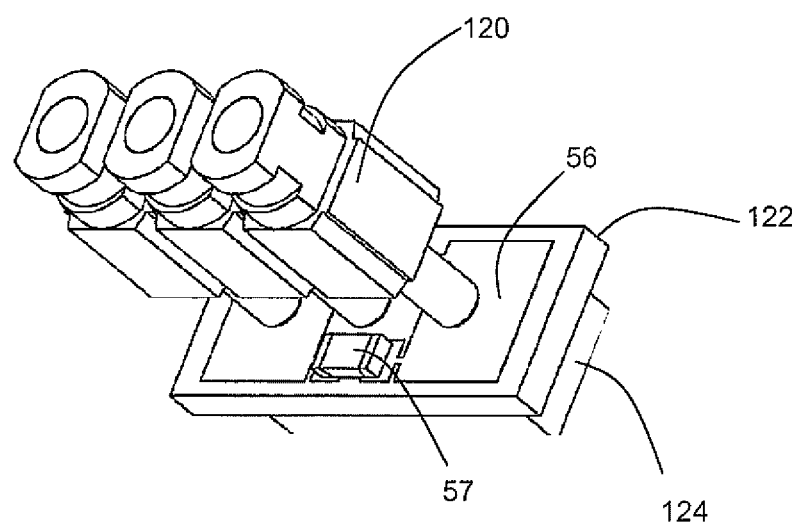

Referring to FIG. 9 (a) an embodiment of a replaceable circuit is illustrated. In this diagram there is a fuse component 53 placed upon a printed circuit board 54 contactable via a spring loaded connector 55. A reference component 110 and POGO pin header 112 is also shown. The fuse may be any surface mountable fuse component such as a SIBA 160016 350 mA fuse or a Littelfuse 0466.250NR 350 mA fuse. The spring loaded connector may be a MILL-MAX 810-22-003-40-001101 spring loaded header. Both sides of the PCB are connected using conductive VIAs 56. The VIAs 56 may be configured to provide parallel connection or series/parallel configurations to realize the circuit described in FIG. 4.

Referring to an alternative view illustrated in FIG. 9 (b) the spring loaded connector 55 contacts a printed conductive landing pad 56 on the PCB 122 which connects to the reuse mitigation element 57. A POGO pin header 120 and fuse 124 are also shown. The central spring load pin is not used requiring only two connections to be made.

Figure 10:
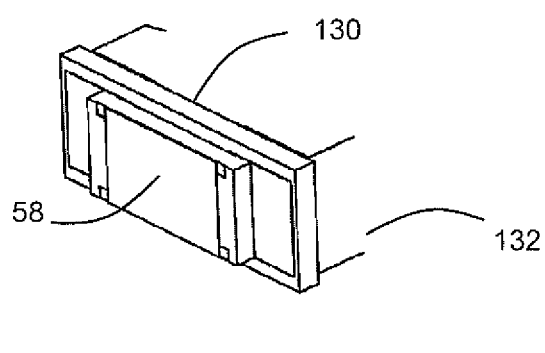
FIG. 10(a) is an illustration of an alternative arrangement of a presence/status/identity and reuse prevention circuit according to some embodiments of the invention.
FIG. 10(b) is an illustration of an alternative arrangement of a presence/status/identity and reuse prevention component assembly using a stacked manufacturing process.
Figure 10:
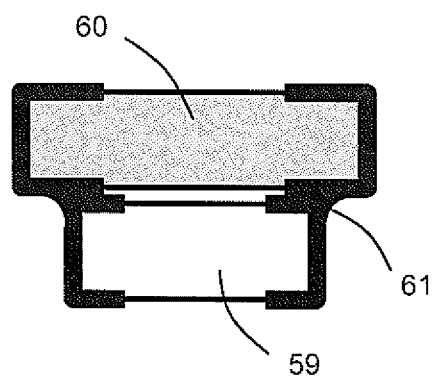
Figure 11:
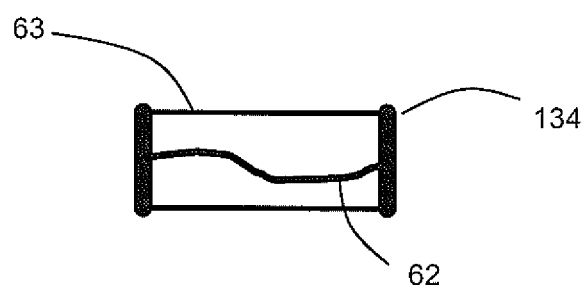
FIG. 11 is an illustration of an alternative arrangement of a presence/status/identity and reuse prevention component assembly using a printed technique to create a resistor/fuse/inductor.

As illustrated in FIG. 10 (a), which shows a PCB 130 and fuse 132, the reuse mitigation element may be any size or type of surface mount packaged component 58 such as a capacitor or resistor or inductor or other reference element as discussed previously. In an alternative embodiment illustrated in FIG. 10 (b) the reuse mitigation element 59 may be attached directly onto the fuse element 60 by soldering 61 or other surface mount procedure negating the requirement for the PCB 54. Advantageously the reuse mitigation 62 may also be printed onto a fuse 63, as shown in FIG. 11, to save cost. FIG. 11 also shows conductive landing pads 134. For example a resistor or inductor could be printed onto a fuse by a process such as offered by Ohmcraft/Micropen NY. Alternatively using a similar process a low resistance link designed to act as a fuse could be printed onto a surface mount resistor, capacitor or inductor or any other surface mount component intended to act as a reference element as described previously.

Figure 12A:
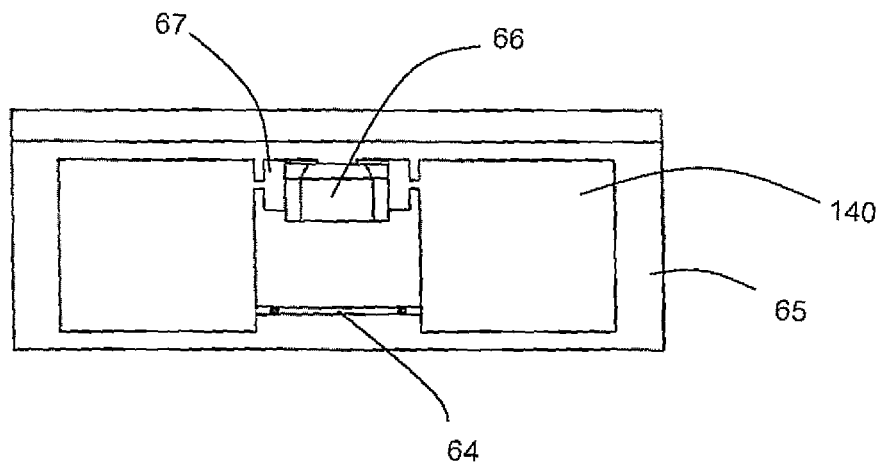
FIG. 12 (a) is an illustration of a presence/status/identity and reuse prevention circuit with integrated printed fuse element according to some embodiments of the invention.
FIG. 12(b) is an illustration of an alternative embodiment of a presence/status/identity and reuse prevention circuit with integrated printed fuse element and printed capacitor according to some embodiments of the invention.
FIG. 12(c) is an illustration of an alternative embodiment of a presence/status/identity and reuse prevention circuit with integrated printed fuse element and printed inductor according to some embodiments of the invention.
Figure 12B:
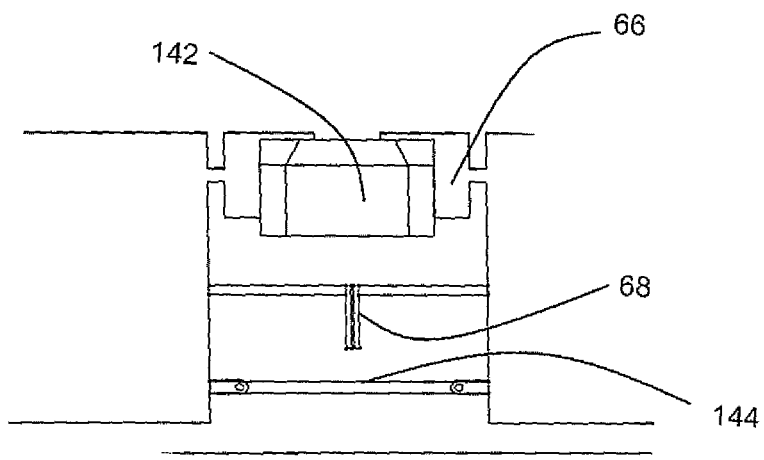
Figure 12C:
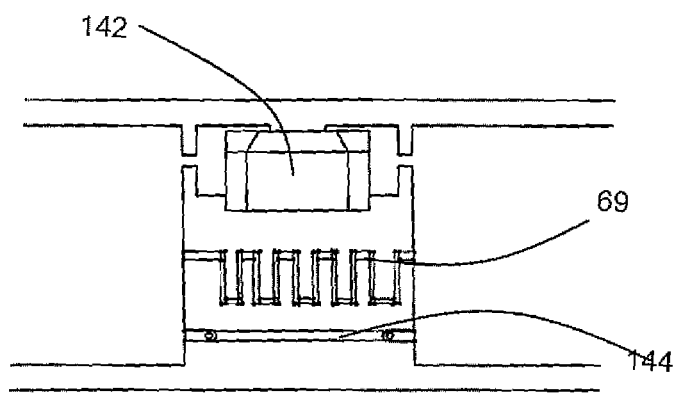

With reference to FIG. 12 (a) an alternative embodiment of a replaceable circuit is illustrated. In this diagram there is a fuse component 64 printed onto the PCB 65, which in this case includes printed PCB landing pads 140. Additionally the reference element 66 is attached to the PCB via landing pads 67. An alternative embodiment of the same circuit is illustrated in FIG. 12 (b) where a capacitive element 68 is printed onto the PCB. A reference element 142 and printed fuse are also shown in FIG. 12 (b). Another alternative embodiment of the same circuit is illustrated in FIG. 12 (c) where an inductive element 69 is printed onto the PCB.

Figure 13:
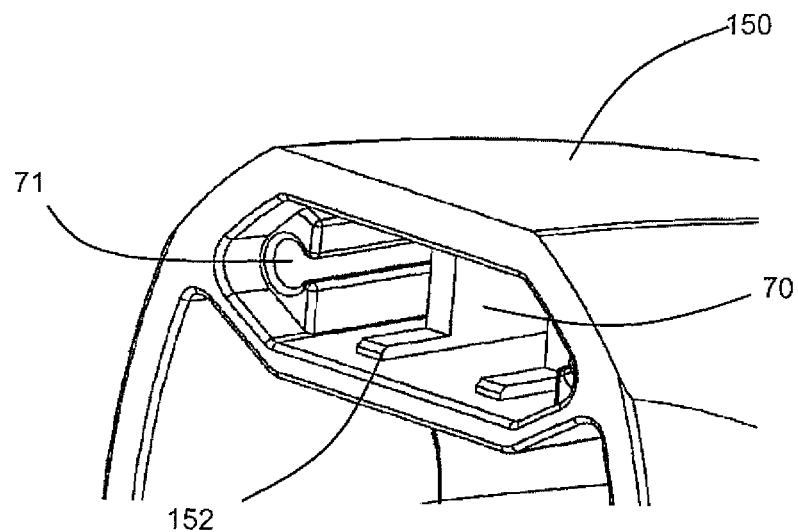
FIG. 13 is an illustration of a housing intended to accommodate a presence/status/identity and reuse prevention circuit according to some embodiments of the invention.
Figure 14:
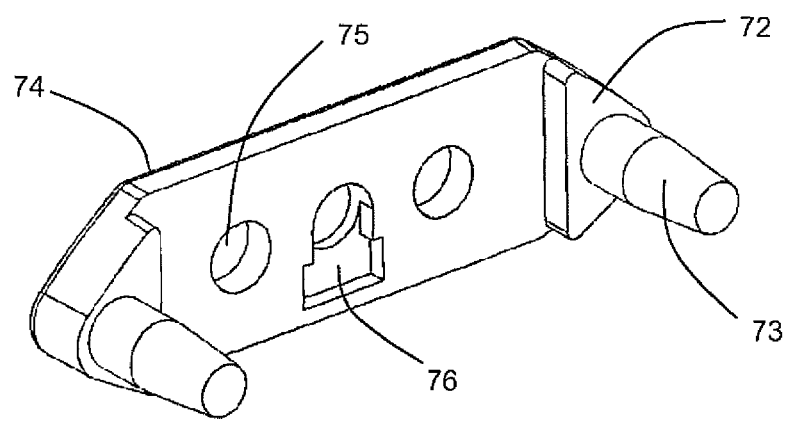
FIG. 14 is an illustration of a covering for a housing intended to accommodate a presence/status/identity and reuse prevention circuit according to some embodiments of the invention.

Referring to FIG. 13, an embodiment of an injection molded housing 150 for a replaceable circuit is illustrated. In this example the replaceable circuit is located against a molded rib 70. A support rib 152 is also shown. A locating hole feature 71 accommodates the connection of a protective covering 72 as illustrated in FIG. 14. In this illustration a locating pin feature 73 mates with a friction fit into the locating hole feature 71. The protective covering 72 has access holes 75 permitting the entry of spring loaded pins. The central spring load pin is not used, however the access hole is provided to balance the forces on all the pins. There is also provided a recessed region 76 that accommodates the surface mounted reference element by way of the design. The protective covering 72 also includes a thin region 74 that may be designed such that any attempt to remove the protective covering could cause this region to fail leaving the locating pin features 73 in situ and preventing removal of the presence/status/identity and reuse prevention circuit. In an alternative embodiment the molded housing as illustrated in FIG. 13 may be filled with a material such as epoxy resin, cyanoacrylate, hot melt, or other solidifying glue that may be used to prevent the removal of the presence/status/identity and reuse prevention circuit.

Figure 15:
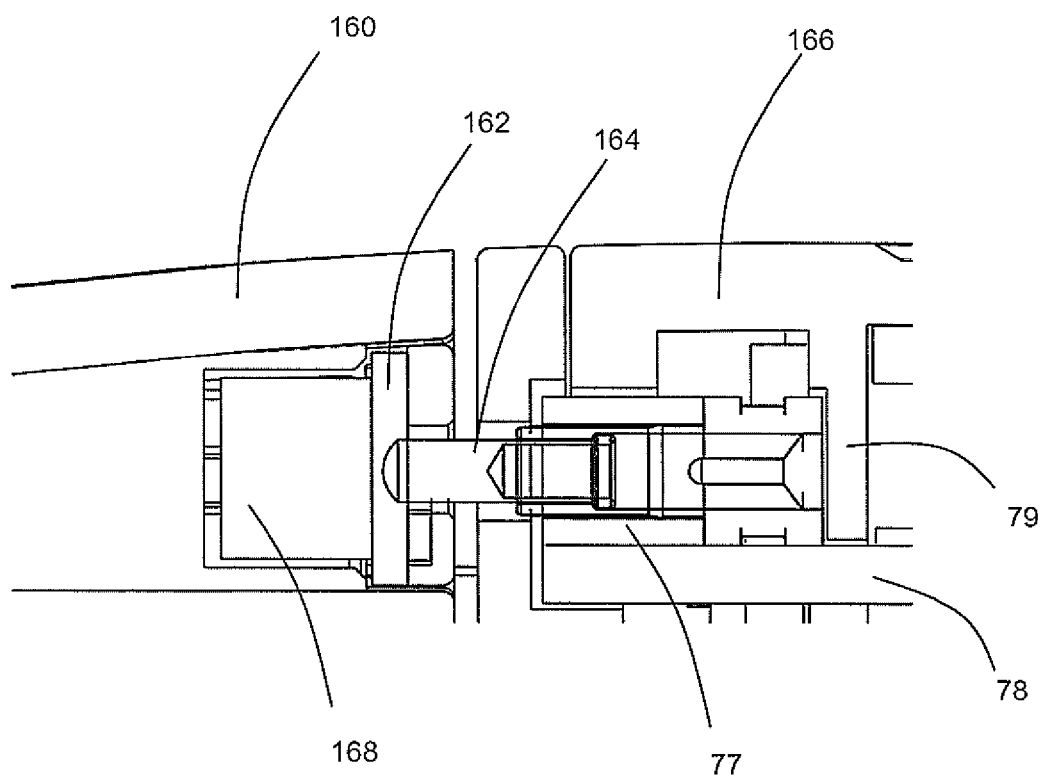
FIG. 15 is a cross-sectional view of the connection mechanism and housing for a presence/status/identity and reuse prevention circuit according to some embodiments of the invention.

Referring to FIG. 15 an embodiment of an injection-molded housing for a replaceable circuit is illustrated. In this illustration the spring loaded pin header 77 is attached to a PCB 78. Advantageously, in order to accommodate manufacturing tolerances the spring loaded pin header 77 is located against a rib 79 as an end stop.

The figure also shows PCB 162, POGO pin 164, plastic housings 160, 166 and fuse 168. The PCB 78 is held at height Z but is not restrained in the X and Y directions. This placement removes the tolerances associated with locating the spring loaded pin header 76 on the PCB 78 which occur in reflow soldering operations which could otherwise affect the reliability of the connection means. Using this technique the tolerances associated with the reliability of the connection are limited to the tightly controlled manufacturing tolerances on the spring loaded pin header and the shrinkage tolerances on the molded plastic parts which are easily accommodated by the spring loaded pin header.

Figure 16:
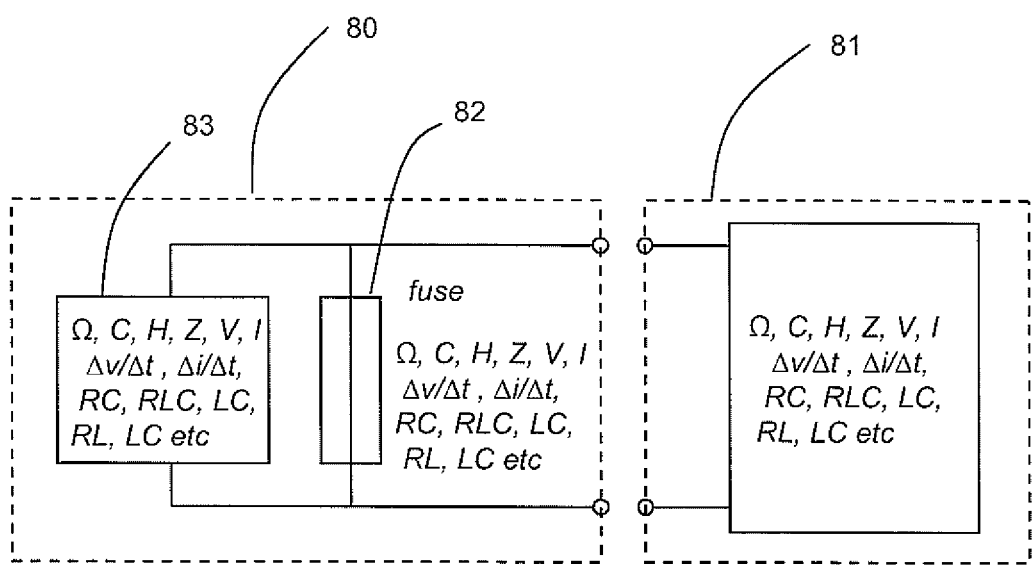
FIG. 16 is a schematic illustration of a system for detecting presence/status/identity and reuse using various electrical characteristic according to some embodiments of the invention.

Referring to FIG. 16 an alternative embodiment of an identity and reuse mitigation system is described. There is a replaceable circuit 80 connectable to controlling system 81 and controlled by a hardware or software algorithm located within the controlling system controlling system 81.

The replaceable circuit 80 having a fusible element 82 to indicate current status and a reference element 83 to confer removal status and unique identity. Using these parameters it can be determined if the connected device is new, has been used, is a particular type, or has been removed during operation. This knowledge may be used to control a treatment or prevent reuse of an expired product. The reference element 83 may be a component or network of components that possess any electrical property such as resistance (Ω), capacitance (C), inductance (H) impedance (Z), breakdown voltage (V), bias (V), current (I) frequency response (RLC) (LC), time constant (RC, RL) delay (RC, RL) or any other electrical characteristic. The system may also make use of other electrical characteristics of the fuse 82 in conjunction with the reference element.

It will be understood that the present invention has been described above purely by way of example, and modifications of detail can be made within the scope of the invention.

Each feature disclosed in the description, and (where appropriate) the claims and drawings may be provided independently or in any appropriate combination.

The invention claimed is:
1. Apparatus for determining a status of a medical device component, wherein the apparatus comprises:
   at least one fusible component to indicate whether the medical device component has been used;
   at least one reference component arranged in parallel with the at least one fusible component and having at least one reference property that is representative of the presence, identity or type of the medical device component, and
   at least one further reference component arranged in series with the at least one fusible component;
   wherein the at least one reference component and the at least one further reference component are each non-fusible under ordinary operating conditions.

2. The apparatus according to claim 1, wherein the at least one fusible component and the at least one reference component are arranged to form a structure in parallel.

3. The apparatus according to claim 1, wherein the at least one fusible component and the at least one reference component are arranged to form a structure so that in operation the value of a measurement of a property is representative of a combination of a property of the at least one fusible component and said reference property of the at least one reference component.

4. The apparatus according to claim 1, wherein the at least one fusible component and the at least one reference component are arranged to form a structure so that in operation it is determined whether the at least one fusible component has fused from the value of a measurement of a property.

5. The apparatus according to claim 4, wherein, if the at least one fusible component has been fused, said at least one reference property of the at least one reference element is determined from the value of the at least one measurement.

6. The apparatus according to claim 4, wherein, if the fusible component has been fused, the value of the at least one measurement is representative of at least one of:—the presence of the medical device component; the identity of the medical device component; the type of the medical device component.

7. The apparatus according to claim 3, wherein the measurement is a measurement of at least one of resistance, capacitance, impedance, breakdown voltage, bias, frequency response, time constant, or delay.

8. The apparatus according to claim 1, wherein there is a measurement path that passes through the at least one reference component.

9. The apparatus according to claim 8, wherein:
the fusible component when not fused provides a short circuit or low resistance path in the measurement path across the or at least one of the reference components; and
the short circuit or low resistance path is removed when the fusible component is fused.

10. The apparatus according to claim 3, wherein, there is a measurement path that passes through the at least one reference component and in operation, the at least one measurement is performed via the measurement path.

11. The apparatus according to claim 1, wherein said reference property comprises at least one of resistance, capacitance, impedance, breakdown voltage, bias, frequency response, time constant, or delay.

12. The apparatus according to claim 1, further comprises a data store storing data representative of the value of the at least one reference property.

13. The apparatus according to claim 1, wherein the reference component and/or the fusible component comprises at least one of a resistor, a capacitor, a diode, a battery, a passive or active element, a semiconductor device or a combination thereof.

14. The apparatus according to claim 1, wherein the apparatus is incorporated in the medical device component.

15. The apparatus according to claim 1, wherein the medical device component comprises at least one of a detachable or disposable component, wherein the medical device component comprises at least one of a microwave applicator or electrosurgery applicator.

16. The apparatus according to claim 1, wherein the medical device component comprises a component that, in normal operation, comes into contact with a patient's body.

17. The apparatus according to claim 1, wherein the medical device component is attachable to a main medical device, and optionally the main medical device comprises at least one of a handpiece or connection terminal connected via cabling to a main controlling system.

18. The apparatus according to claim 1, further comprising a controller comprising a processing resource that is configured to perform an algorithm for determining a status of the medical device component from at least one measurement performed on the at least one fusible component and/or the at least one reference component.

19. A control apparatus for determining the status of a medical device component, the control apparatus being connectable to, or comprised within, the apparatus according to claim 1, and comprising a processing resource that is configured to perform an algorithm for determining a status of the medical device component from at least one measurement performed on the at least one fusible component and/or the at least one reference component.

20. The apparatus according to claim 19, further comprising measurement circuitry that performs the at least one measurement, wherein the measurement circuitry comprises measurement circuitry that performs at least one of electrical or magnetic measurements.

21. The apparatus according to claim 20, wherein there is a measurement path that passes through the at least one reference component, and the measurement circuitry is configured to perform the at least one measurement via the measurement path.

22. The apparatus according to claim 19, wherein the medical device component is connectable to a main medical device and the algorithm is configured to control operation of the main medical device in dependence on the determined status of the medical device component.

23. The apparatus according to claim 19, wherein the controller is configured to at least one of determine if the medical device component has been connected or disconnected, or determine if the medical device component has been used or is unused; and
to control operation of the main medical device in dependence on the determination.

24. The apparatus according to claim 19, wherein the controller is configured to determine whether the fusible element has been fused and prevent use of the main medical device if the fusible element has been fused.

25. The apparatus according to claim 19, wherein the controller is configured to determine whether the medical device component has been used and prevent reuse of the medical device component.

26. The apparatus according to claim 19, wherein the controller is configured to determine whether the fusible element has been fused, and if the fusible element has not been fused to apply a signal to fuse the fusible element.

27. The apparatus according to claim 19, wherein the controller is configured to identify the type or identity of the medical device component and to select at least one operating parameter in dependence on the type of identity of the medical device component.

28. The apparatus according to claim 19, wherein the algorithm monitors the length of time the medical device component has been used or has been useable, wherein the length of time includes at least one of the length of time since the medical device component was attached to the main medical device or the length of time since the fusible component was fused.

29. The apparatus according to claim 19, wherein the algorithm is configured to monitor the number or length of treatments performed using the medical device component.

30. The apparatus according to claim 19, wherein the algorithm is configured to allow use of the medical device component for a selected period of time or for a selected number of treatments.

31. The apparatus according to claim 19, wherein the algorithm is configured to prevent normal operation of the main medical device and/or the medical device component in response to expiry of the selected period of time and/or in response to performance of the selected number of treatments.

32. The apparatus according to claim 19, wherein the controller is configured to monitor disconnection of the medical device component from the main medical device and to allow disconnection for times shorter than a selected time period without preventing operation of the main medical device.

33. A method of operating a medical device comprising attaching an apparatus according to claim 1 to the medical device, determining the status of a medical device component using the apparatus, and operating the medical device in dependence on the determined status.

34. A method for determining a status of a medical device component, wherein the method comprises performing a measurement via a measurement path, the measurement path comprising:

at least one fusible component to indicate whether the medical device component has been used, at least one reference component arranged in parallel with the at least one fusible component and having at least one reference property that is representative of the presence, identity or type of the medical device component, the at least one reference component is non-fusible under ordinary operating conditions, and at least one further reference component arranged in series with the at least one fusible component, wherein the at least one reference component and the at least one further reference component are each non-fusible under ordinary operating conditions.

* * * * *